United States Patent [19]

Steiniger et al.

[11] Patent Number: 4,702,803
[45] Date of Patent: Oct. 27, 1987

[54] PREPARATION OF PYRAZOLES

[75] Inventors: Michael Steiniger, Neustadt; Eckhard Stroefer, Mannheim, both of Fed. Rep. of Germany

[73] Assignee: BASF Aktiengesellschaft, Ludwigshafen, Fed. Rep. of Germany

[21] Appl. No.: 4,971

[22] Filed: Jan. 20, 1987

[30] Foreign Application Priority Data

Feb. 5, 1986 [DE] Fed. Rep. of Germany ....... 3603376

[51] Int. Cl.$^4$ .............................................. C25B 3/02
[52] U.S. Cl. .................................... 204/59 R; 204/78
[58] Field of Search ................................ 204/59 R, 78

[56] References Cited

FOREIGN PATENT DOCUMENTS 48373 of 1982 European Pat. Off. .
45394 of 1982 European Pat. Off. .
162247 of 1985 European Pat. Off. .
3209148 of 1983 Fed. Rep. of Germany .

OTHER PUBLICATIONS

Adv. Heterocycl. Chem. 6 (1966), p. 385.
The Chemistry of Heterocyclic Compounds, vol. 22 (1967), pp. 41–49.
Z. Chem. 14 (1974), p. 236.
Katritzky, Advances in Heterocyclic Chemistry; Academic Press; N.Y., N.Y.; vol. 36, pp. 305–307.

*Primary Examiner*—Arthur P. Demers
*Attorney, Agent, or Firm*—John H. Shurtleff

[57] ABSTRACT

Pyrazoles of the general formula

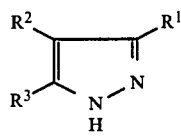

I where $R^1$, $R^2$ and $R^3$ are each hydrogen, alkyl, cycloalkyl or aryl, are prepared by electrochemical oxidation of 2-pyrazolines of the general formula

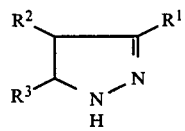

II in the presence of an ionic halide.

10 Claims, No Drawings

PREPARATION OF PYRAZOLES

The present invention relates to a new process for preparing pyrazoles by electrochemical oxidation of 2-pyrazolines.

It is known that pyrazoles can be prepared by oxidizing 2-pyrazolines with oxidizing agents such as, for example, bromine (Adv. Heterocycl. Chem. 6 (1966), 385), chlorine and hydrochlorites (EP-B-48,373), potassium permanganate, nitric acid, air, lead tetraacetate or chromium trioxide (The Chemistry of Heterocyclic Compounds, Volume 22, pp. 41–49 (1967)) or peroxides (EP-A-162,247). The dehydrogenation of pyrazolines to the corresponding pyrazoles is possible according to EP-B-45,394 and DE-A-32 09 148 with sulfur and selenium respectively or over catalysts of platinum metals in the gas phase.

The disadvantages with these known processes, are the use of costly and/or toxic oxidizing agents, the disposal of the products formed from the oxidizing agents, and, for safety reasons, the complicated reaction management.

It is an object of the present invention to provide a process for preparing pyrazoles which is simpler and more economical to carry out and is enviromentally especially acceptable.

We have found that this object is achieved with a process for preparing a pyrazole of the general formula I

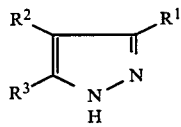

where $R^1$, $R^2$ and $R^3$ are each hydrogen, alkyl, cycloalkyl or aryl, by electrochemically oxidizing a 2-pyrazoline of the general formula II

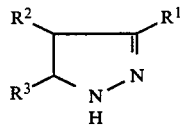

where $R^1$, $R^2$ and $R^3$ each have the abovementioned meanings, in the presence of an ionic halide.

The reaction of the process according to the invention can be described by the following formulae:

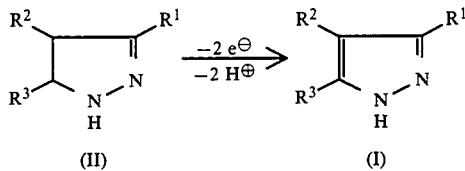

The advantageous result of the process according to the invention is surprising since hitherto the only 2-pyrazolines which could be anodically oxidized to pyrazoles had a N-aryl group to stabilize the free radical cation intermediate. Even then the electrochemical oxidiation of, for example, 1-phenyl-2-pyrazoline to the corresponding pyrazole was only possible in the presence of a base, such as pyridine. In the absence of a base the dimer bis[1-phenyl-2-pyrazolin-3-yl] was formed (Z. Chem. 14 (1974), 236 or Advn. Heterocycl. Chem. 36 (1984), 237).

In the 2-pyrazolines of the formula II which are used as starting materials, $R^1$, $R^2$ and $R^3$ are each hydrogen, alkyl, cycloalkyl or aryl. Alkyl contains for example from 1 to 12, preferably from 1 to 8, in particular from 1 to 4, carbon atoms, such as methyl, ethyl, n- and i-propyl, n-butyl or tert.—butyl. Examples of cyclo-alkyl are those of 3 to 8, in particular 5 or 6, carbon atoms. Aryl is, for example, phenyl. Aryl may carry substituents which are inert under the reaction conditions, such as alkyl or alkoxy of up to 4 carbon atoms, halogen or nitrile.

Specific examples of compounds of the formula II are: 2-pyrazoline, 3-methyl-2-pyrazoline, 4-phenyl-2-pyrazoline, 4-methyl-2-pyrazoline and 4,5-dimethyl-2-pyrazoline.

The starting compounds of the formula II can be prepared for example in a conventional manner by reacting hydrazine with $\alpha,\beta$-unsaturated aldehydes such as acrolein or appropriately substituted acroleins.

Suitable ionic halides are salts of hydroiodic, hydrobromic and hydrochloric acid or these acids themselves. Particular preference is given to the salts of hydrobromic acid, such as alkali metal and alkaline earth metal bromides and quaternary ammonium, in particular tetraalkylammonium bromides. The cation is not an essential feature of the invention; therefore it is also possible to use other ionic metal halides, but inexpensive halides are expediently chosen. Examples are sodium bromide, potassium bromide, calcium bromide, ammonium bromide and di—, tri— and tetramethylammonium or tetraethylammonium bromide. For the electrooxidation it is expedient to use a solution of the pyrazoline and the ionic halide in a suitable solvent. Suitable solvents are those which prove sufficiently stable under the electrolysis conditions. This condition is met, for example, by ethers, such as tetrahydrofuran, chlorohydrocarbons, such as methylene chloride, ketones, such as acetone, and nitriles, such as acetonitrile. Particularly suitable are alcohols, such as methanol and ethanol.

The composition of the electrolyte can be chosen within wide limits. For instance, the electrolyte comprises an alcoholic solution of the 2-pyrazoline of the general formula II with a 2-pyrazoline content of from 1 to 30, preferably from 3 to 15, % by weight and an ionic halide content of from 0.1 to 20, preferably from 1 to 10, % by weight.

The process according to the invention can be carried out in a conventional industrial electrolysis cell. Preference is given to using undivided flow cells which, to minimize the cell voltage, expediently permit low electrode spacings of, for example, from 0.25 to 2 mm. The anode is a noble metal, titanium doped with a noble metal oxide, a metal oxide, such as $MnO_2$ or $PbO_2$, but preferably graphite. The cathode materials are for example lead, iron, steel, nickel or noble metals such as platinum. The preferred cathode material is likewise graphite.

The electrolysis is carried out for example with from 1 to 4 F/mol, preferably from 1.5 to 3 F/mol, of 2-pyrazoline. The current density is not a limiting factor and ranges for example from 0.1 to 25 A/dm², preferably from 3 to 15 A/dm². The process according to the invention is carried out for example within a temperature range from 10° C. to a temperature which is 5° C. below the boiling point of the solvent used. If methanol or ethanol is used, the electrolysis is carried out at atmospheric pressure at 10°-40° C. The electrolysis can be carried out not only batchwise but also continuously.

The electrolyzed mixtures can be worked up in a conventional manner. Expediently the electrolyte mixture is worked up by distillation. Excess solvent is distilled off first. The halogens are separated off in a conventional manner, for example by filtration or extraction, and the product is purified by distillation or recrystallization. The solvent, any unconverted 2-pyrazoline and halides can advantageously be recycled for electrolysis.

The pyrazoles of the general formula I which are obtained by the process according to the invention are versatile intermediates for the synthesis of dyes, pharmaceutical agents and crop protection agents.

EXAMPLES

The elctrooxidations were carried out in an undivided electrolysis cell containing 6 graphite electrodes (5 gaps, electrodes spacing from 0.5 to 1 mm). During the electrolysis, the electrolyte, decomposition of which is disclosed in Examples 1 to 7, was pumped through the cell via a heat exchanger at a rate of 200 l/h.

EXAMPLE 1

A solution of 117 g of 2-pyrazoline and 64 g of NaBr in 3,000 g of methanol was electrolysed with 2 F/mol of 2-pyrazoline at a current density of 4.8 A/dm$^2$ and 10° C. Analysis by gas chromatography showed that the electrolysed mixture contained 62 g of pyrazole and 18.6 g of unconverted 2-pyrazoline. This corresponds to a conversion of 83%, a yield of 55% and a selectivity of 65%. Methanol was distilled out of the electrolysed mixture under atmospheric pressure at a bottom temperature of up to 100°-110° C. The residue was freed of bromide and purified by distillation at 90°-105° C. and 50 mbar. 16 g of 2-pyrazoline and 58.1 g of pyrazole, corresponding to a yield of 50% and a selectivity of 58%, were isolated.

EXAMPLE 2

A solution of 295 g of 2-pyrazoline and 53 g of NaBr in 2,600 g of methanol was electrolysed with 2 F/mol of 2-pyrazoline at a current density of 6.8 A/dm$^2$ and 20° C. From the analysis by gas chromatography the conversion was found to be 84%, the yield 50% and the selectivity 61%.

EXAMPLE 3

117 g of 2-pyrazoline and 64 g of KBr were dissolved in 3,000 g of methanol and electrolysed with 2 F/mole of 2-pyrazoline at a current density of 9 A/dm$^2$ and 15° C. Analysis of the electrolysed mixture by gas chromatography found 9.5 g of unconverted 2-pyrazoline and 66 g of pyrazole. From this the conversion can be calculated to be 92%, the yield 58% and the selectivity 63%.

EXAMPLE 4

A solution of 117 g of 2-pyrazoline and 64 g of tetraethylammonium bromide in 3,000 g of methanol was electrolysed with 2 F/mol of 2-pyrazoline at a current density of 9 A/dm$^2$ and 40° C. Analysis of the electrolysed mixture by gas chromatography found 30.8 g of 2-pyrazoline and 68 g of pyrazole. From this it is possible to calculate the pyrazole yield as 60%, the conversion as 74% and the selectivity as 81%. 66 g of pyrazole (58% yield, 78% selectivity) were isolated by fractional distillation at 99° C. and 50 mbar.

EXAMPLE 5

234 g of 2-pyrazoline and 64 g of tetraethylammonium bromide were dissolved in 3,000 g of ethanol and electrolyzed with 2 F/mol of 2-pyrazoline at a current density of 6.8 A/dm$^2$ and 30° C. Working up as described in Example 1 gave 18.2 g of 2-pyrazoline and 129 g of pyrazole. This corresponds to a conversion of 92%, a yield of 57% and a selectivity of 62%.

EXAMPLE 6

A solution of 100 g of 3-methyl-2-pyrazoline and 64 g of NaBr in 3,000 g of methanol was electrolysed with 2 F/mol of 3-methyl-2-pyrazoline at a current density of 6.8 A/dm$^2$ at a temperature of 20° C. Customary working up of the electrolysed mixture and fractional distillation gave 24.5 g of 3-methyl-2-pyrazoline and 29.5 g of 3-methylpyrazole (boiling point 127°-131° C./98 mbar). This corresponds to a conversion of 75%, a yield of 30% and a selectivity of 40%.

EXAMPLE 7

A solution of 146 g of 4-phenyl-2-pyrazoline and 64 g of KBr in 3,000 g of methanol was electrolyzed with 2 F/mol of 4-phenyl-2-pyrazoline at a current density of 9 A/dm$^2$ and 20° C. Analysis by gas chromatography revealed that the electrolysed mixture contained 28.5 g of 4-phenyl-2-pyrazoline and 72 g of 4-phenylpyrazole. The yield of 4-phenylpyrazole is accordingly 50%, the selectivity 63% and the conversion 80%.

We claim:

1. A process for preparing a pyrazole of the general formula

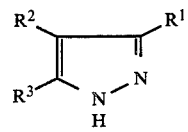

I where R$^1$, R$^2$ and R$^3$ are each hydrogen, alkyl, cycloalkyl or aryl, which comprises electrochemically oxidizing a 2-pyrazoline of the general formula

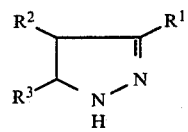

II where R$^1$, R$^2$ and R$^3$ have the abovementioned meanings, in the presence of an ionic halide.

2. A process as claimed in claim 1, wherein the ionic halide is a salt of hydrochloric or hydrobromic acid.

3. A process as claimed in claim 1, wherein the electrolysis is performed with graphite anodes.

4. A process as claimed in claim 1, wherein the electrooxidation is performed on a solution of the 2-pyrazoline and the ionic halide in a solvent which is stable under the electrolysis conditions.

5. A process as claimed in claim 4, wherein the 2-pyrazoline is used in the form of an alcoholic solution which contains from 1 to 30% by weight of the 2-pyrazoline and from 0.1 to 20% by weight of the halide.

6. A process as claimed in claim 4, wherein the solvent is an ether, a hydrocarbon, a ketone, a nitrile or an alcohol.

7. A process as claimed in claim 4, wherein the solvent is methanol or ethanol.

8. A process as claimed in claim 1, wherein the electrolysis is carried out with from 1 to 4 F/mol of 2-pyrazoline.

9. A process as claimed in claim 1, wherein the electrolysis is carried out at current densities of from 0.1 to 25 A/dm$^2$.

10. A process as claimed in claim 4, wherein the electrolysis is carried out within a temperature range of from 10° C. to a temperature which is 5° C. below the boiling point of the solvent used.

* * * * *